US006478759B1

(12) United States Patent
Modglin et al.

(10) Patent No.: US 6,478,759 B1
(45) Date of Patent: Nov. 12, 2002

(54) THORACO-LUMBO-SACRAL ORTHOSIS

(75) Inventors: Michael D. Modglin, Braselton, GA (US); Paul Jackovitch, Lawrenceville, GA (US)

(73) Assignee: DeRoyal Industries, Inc., Powell, TN (US)

( * ) Notice: Subject to any disclaimer, the term of this patent is extended or adjusted under 35 U.S.C. 154(b) by 0 days.

(21) Appl. No.: 09/521,562

(22) Filed: Mar. 9, 2000

(51) Int. Cl.$^7$ ................................................ A61F 5/00
(52) U.S. Cl. ...................................... 602/19; 128/100.1
(58) Field of Search .................... 602/5, 19; 128/100.1, 128/96.1, 99.1, 846

(56) References Cited

U.S. PATENT DOCUMENTS

| | | | |
|---|---|---|---|
| 3,292,616 A | * 12/1966 | Freeman ...................... | 602/19 |
| 4,120,297 A | * 10/1978 | Rabischong .................. | 602/19 |
| 4,489,676 A | * 12/1984 | Colquist ...................... | 602/19 |
| 4,821,739 A | 4/1989 | Willner et al. | |
| 5,437,614 A | 8/1995 | Grim | |
| 5,537,690 A | 7/1996 | Johnson | |
| 5,853,378 A | * 12/1998 | Modglin .................. | 128/100.1 |
| 5,967,998 A | * 10/1999 | Modglin ....................... | 602/19 |

FOREIGN PATENT DOCUMENTS

WO     WO 99/65428     12/1999

OTHER PUBLICATIONS

Declaration of Michael D. Modglin.
Pictures Fetherlite brace made by National Orthotic Laboratories, Inc., bearing Patent No. 4.508.110, sold 1994.
National Orthotic Laboratories, Inc. catalog, 1994.
Pictures Mirage prototype brace made by Michael D. Modglin, 1995.
Pictures Kittle prototype; brace made by Michael D. Modglin, 1995.
Letter Mike Modglin to Mr. Jerry Kittle, Nov. 8, 1995.

* cited by examiner

Primary Examiner—Michael A. Brown
(74) Attorney, Agent, or Firm—Smith, Gambrell & Russell, LLP

(57) ABSTRACT

A thoraco-lumbo-sacral brace formed of flexible materials designed to fit patients of varying shapes and sizes. The brace comprises an anterior support and a posterior support, both made of a hook and loop material, and connected by two sets of connection straps. The connection straps comprise a series of flexible straps attached to a common strap, and a rigid strap. Each flexible strap passes through a loop attached to the posterior support. The common strap is made of a hook and loop material The common strap may be fastened to the anterior support at any angle in order to tighten the brace and adjust it to fit a variety of body types. The rigid strap similarly passes through a loop and is attached to the anterior support atop the common strap, thereby minimizing unwanted lateral motion. The anterior support further may accept a plurality of splints sized to fit within a plurality of cavities located on the front side of the anterior support. These splints provide additional support for the patient. Lateral panels may be attached between the anterior support and posterior support to widen the brace. A thoracic lumbar support may be attached to the posterior support, providing increased support for a patient's upper back. A sternal extension may be attached to the anterior support, thus providing additional bracing for a patient's chest.

23 Claims, 4 Drawing Sheets

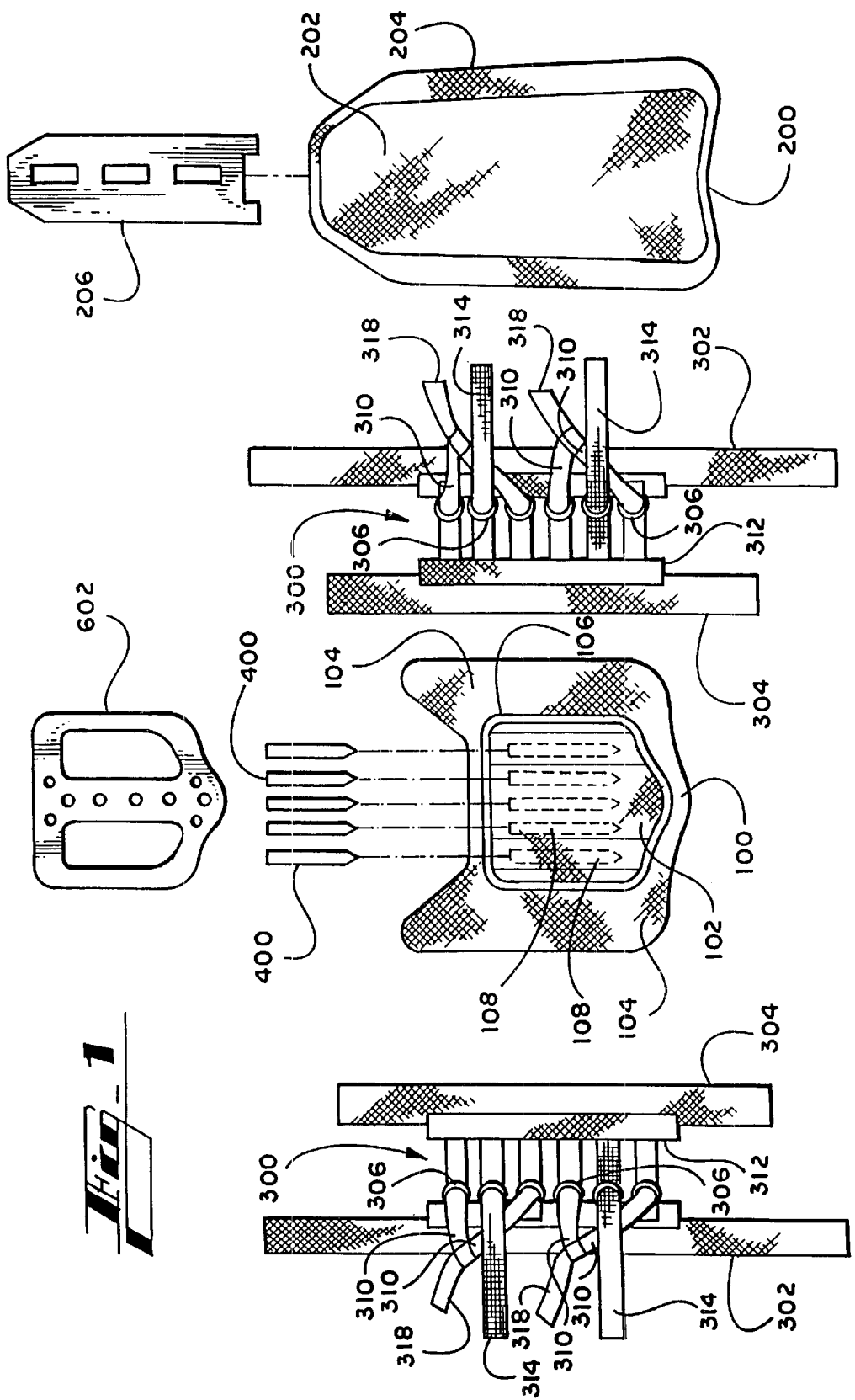

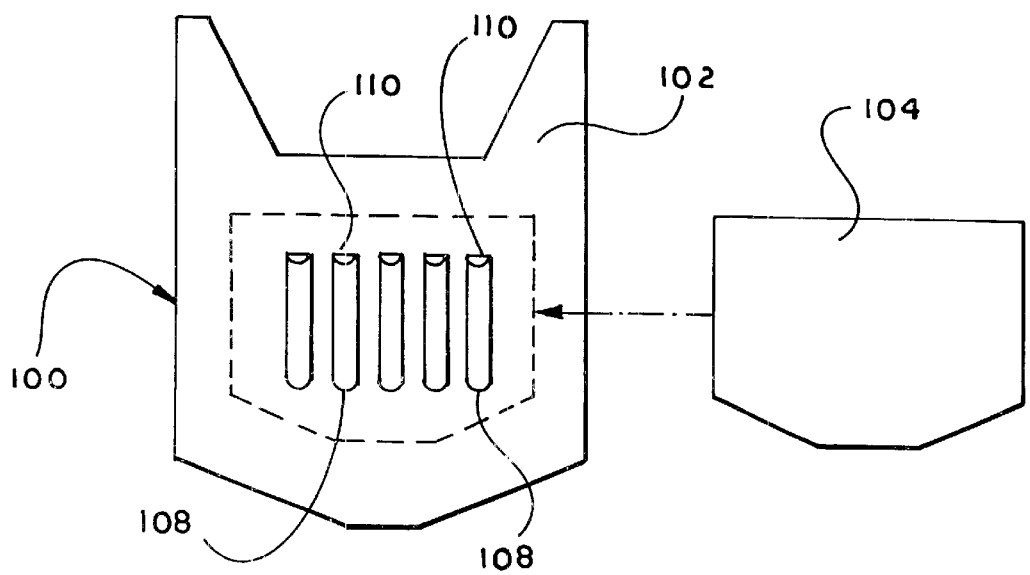
FIG_1A
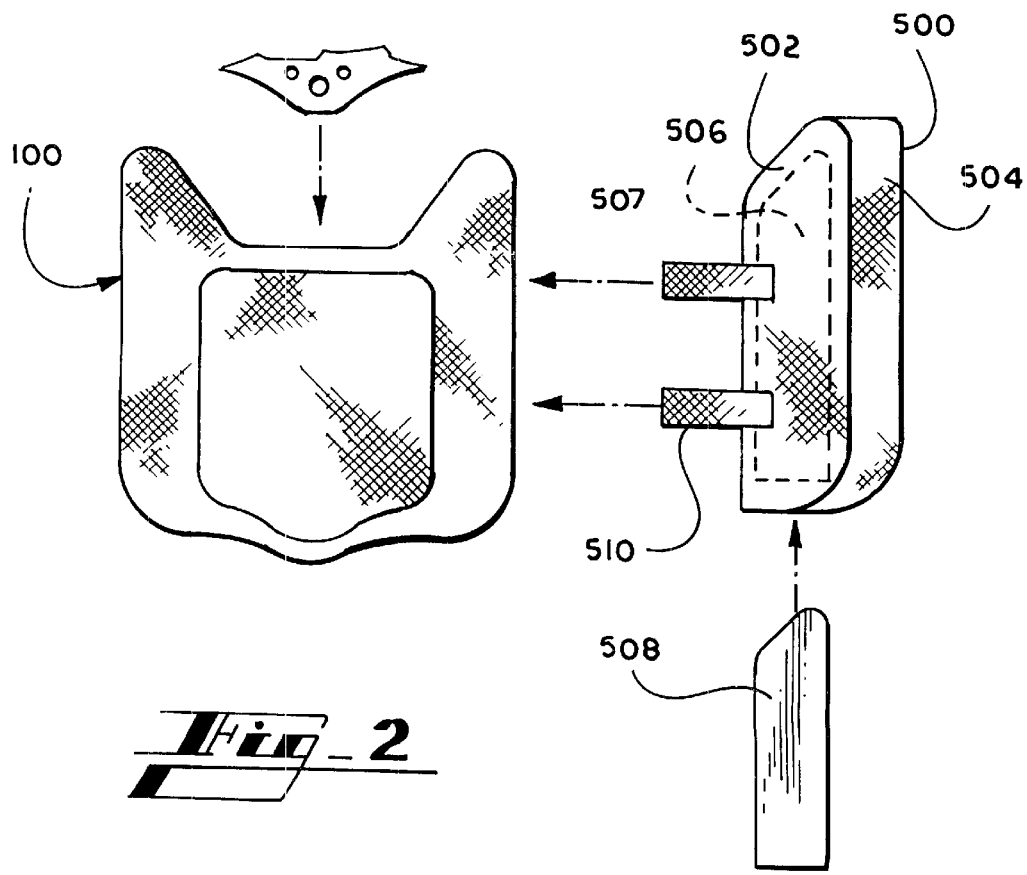
FIG_2

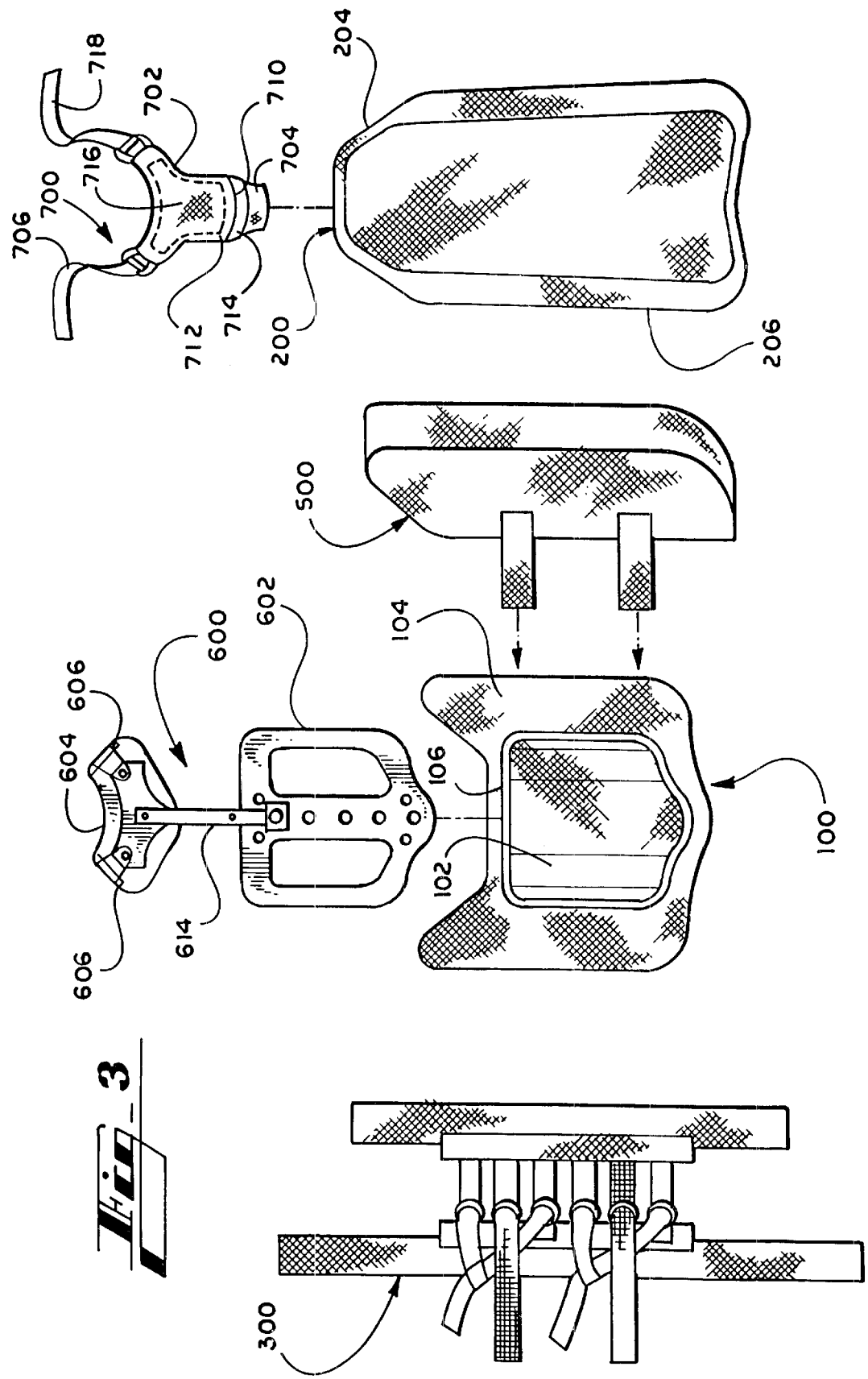

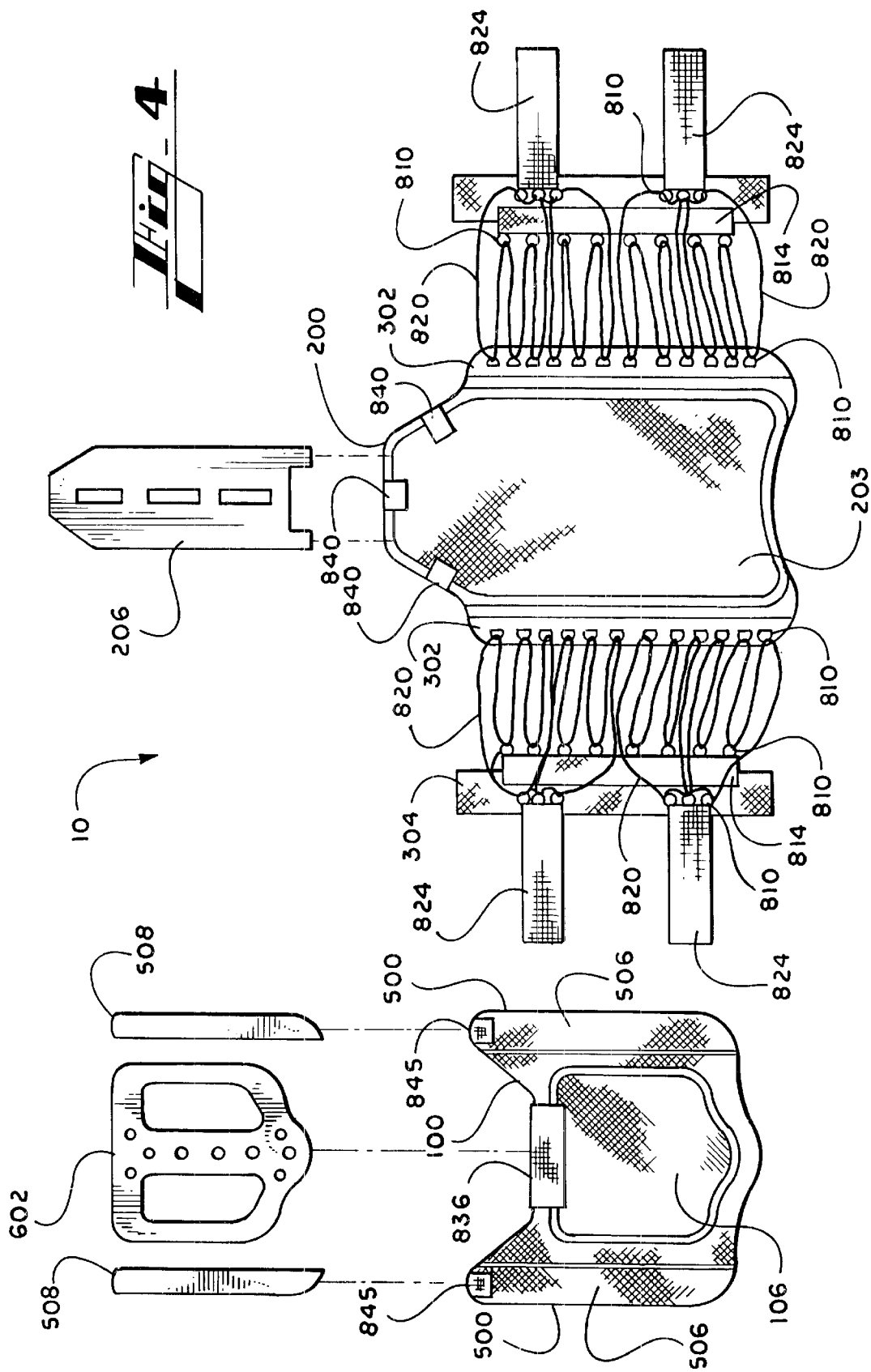

THORACO-LUMBO-SACRAL ORTHOSIS

TECHNICAL FIELD

The present invention relates to a thoraco-lumbo-sacral orthosis for supporting a patient's back and spine, and more particularly relates to a flexible adjustable brace that may be quickly and individually tailored to a patient's physique and condition.

BACKGROUND

Various types of body braces have been used for many years to aid in the rehabilitation of the spine. These braces traditionally comprise rigid bodies having integrated splints. Due to the limitations of these types of braces, elderly, disabled, and severely injured persons often experience great difficulty in adjusting, fastening, and wearing these types of body braces.

One alternative to rigid body braces are soft, flexible body braces. The typical flexible body brace uses corset lacings and buckles or snaps to fasten together the various portions of the brace. The corset lacings, buckles, or snaps require constant adjustment to provide maximum comfort and support for the wearer. Further, buckles and snaps may only be adjusted in quantum increments, much like a belt. If the zone of maximum comfort for a patient falls between two adjustment levels, the patient is forced to choose a setting for the brace that is either too tight or too loose.

Flexible braces that do not employ a snap or buckle fitting often suffer from additional problems. First, many flexible braces are only manufactured in specific sizes and typically do not include sizes for larger people. Second, due to their very nature, many flexible braces fail to adequately control lateral motion. In particular, the brace fittings may comprise soft flexible straps that stretch or constrict excessively when the patient moves. The stretching or constriction of these straps may cause the fit of the brace to become improper, thereby prolonging the patient's recovery.

Additionally, most braces only provide one set level of support for a patient. The brace either incorporates a rigid splint member into the fittings for support, or may have a single removable splint. However, many patients find that their need for back support diminishes as they heal, and that a brace that continues to provide the initial level of support throughout the patient's recuperation quickly becomes uncomfortable. Further, the typical back brace only supports the lower back and chest, and fails to provide any support for the upper portions of the back.

Thus, there is a need for a soft, flexible thoraco-lumbo-sacral brace that may be easily adjusted to fit a variety of body shapes and sizes. There is a further need for a brace that provides varying levels of back support, according to the rehabilitative needs of the patient and the patient's rate of healing. There is also a need for a back brace that provides adequate support for the thoracic and lumbar regions of the back. Finally, there is a need for a brace that provides adequate lateral support in order to minimize unwanted lateral torso motion.

SUMMARY

The present invention satisfies the needs identified above. The invention comprises a thoraco-lumbo-sacral orthopedic brace which may be easily and quickly adjusted to fit varying body types though the use of flexible connection straps. A rigid strap placed over the flexible straps serves to minimize undesired lateral torso motion. Lateral panels may be added to the brace to further expand its size and allow for fitting of large patients. Varying levels of back support are provided through the use of a plurality of removable splints. The splints may be added or removed as necessary to match a patient's support requirements. A thoracic lumbar support dorso-lumbar extension and sternal pad extension unit add additional bracing for the upper back and chest.

Generally described, the present invention provides a thoraco-lumbo-sacral orthopedic brace apparatus formed of flexible materials to fit patients of varying heights and sizes. The brace comprises a flexible anterior support with a large cavity sized to receive a rigid splint. The rigid splint provides back support beyond that provided by the brace alone. Located within the large cavity are multiple smaller cavities sized to receive a series of smaller splints. Each small cavity may contain a single smaller splint. These smaller splints may be used singly or in combination to provide varying degrees of support for a patient, according to the patient's individual needs. The smaller splints may be used simultaneously with the single large splint in the case where a patient needs a significant amount of back support. The brace may also comprise a posterior support that is similar to the anterior support.

The brace's anterior and posterior flexible supports are formed of a hook and loop material, and are connected by a set of connecting straps. The connecting straps are also formed of a hook and loop material. A plurality of flexible connecting straps are attached to a second crossbar, which is in turn attached to the anterior support. The flexible straps pass through a plurality of loops connected to a first crossbar, which is in turn attached to the posterior support. The flexible straps are folded over on themselves and attached via the hook and loop material to the anterior support, thus tightening and connecting the various portions of the brace. Because each of the connecting straps is formed of the hook and loop material, any portion of any strap may be attached to the anterior support. A rigid strap is also attached to the first crossbar and passes through a loop attached to the second crossbar. The rigid strap passes over the flexible straps and is affixed to the anterior support. This rigid strap minimizes the flexibility and give of the flexible straps, thus minimizing unwanted torso motion while retaining the brace's ability to be adjusted to a wide variety of body shapes and sizes. Conventional corset lacing using parachute cord can also be used to help prevent unwanted torso motion.

Flexible lateral panels may be incorporated into the brace in order to further expand its size. The lateral panels are curved to follow the natural curve of a patient's side and are formed of hook and loop material. The panel is attached to the anterior support of the brace, and the connector straps connect to the anterior support. In this manner, the circumference of the brace is expanded by the width of the lateral stays. The flexible lateral panels further have a cavity sized to contain a removable rigid splint. The removable rigid splint affords a higher level of support to a patient than does a conventional flexible brace.

The lumbo-sacral brace may further comprise a thoracic lumbar support and sternal extension to provide support for the upper back and chest. The thoracic lumbar support consists of a soft, flexible y-shaped body, a pair of flexible straps, a bottom flap, and a cavity. The bottom flap is formed of a hook and loop material in order to allow a patient to attach the thoracic lumbar support to any portion of the posterior support at any height. The cavity may contain a rigid splint in order to provide enhanced bracing to the upper back. A pair of flexible straps connects the thoracic lumbar support to the sternal extension.

The sternal extension may be removably attached to the anterior portion to abut the collarbone of a patient. A pair of loops is attached to the u-shaped padded body which rests against the chest wall. The flexible straps of the thoracic lumbar support are threaded through these loops in order to connect the two supports. The padded body of the sternal extension is connected to a rigid insert by a connector bar. The connector bar may be adjusted to vary the distance between the body and the insert, thus accounting for patients of different heights. The rigid insert is placed within the large cavity of the anterior support, thus providing additional support to the patient and securing the sternal extension to the brace. The lumbo-sacral brace may further comprise a dorso-lumbar extension piece. This is comprised of the rigid material that is inserted into the pockets and is removable. It is attached using screws and barrel nuts. This produces a dynamic unit that serves to pull the patient into hyper-extension, a position that is desirable for most spine pathologies.

BRIEF DESCRIPTION OF THE DRAWINGS

FIG. 1 depicts a lumbo-sacral brace in accordance with the present invention.

FIG. 1A depicts a sectional view of an anterior support in accordance with the present invention.

FIG. 2 depicts a lateral panel for expansion of a lumbo-sacral brace in accordance with the present invention.

FIG. 3 depicts a thoracic lumbar support and sternal extension in accordance with the present invention.

FIG. 4 depicts another embodiment of a lumbo-sacral brace in accordance with the present invention.

DETAILED DESCRIPTION OF ILLUSTRATIVE EMBODIMENTS

The present invention is directed to a lumbo-sacral orthosis or brace for limiting or controlling the motion in the thoracic and lumbo-sacral areas of the spine of a patient.

The brace provides enhanced support for a patient's back. The anterior and posterior supports comprising the brace are made of a soft, breathable material with a foam core for the comfort of the patient. The size of the brace may be adjusted to fit any size patient through the use of flexible connection straps and lateral expansion panels. The flexible straps permit the brace to expand to any size, rather than forcing the brace to expand in steps as with snaps or buckles. Lateral stays may also contain a rigid splint to provide side support in addition to expanding the brace size. A rigid strap may be fastened over the flexible straps in order to minimize unwanted side motion resulting from the use of flexible straps instead of a stiff binding. A thoracic lumbar support may be added to the back of the brace in order to support a patient's upper back. A sternal extension similarly may provide additional support for a patient's chest. The level of support provided by the brace may be individually tailored to a patient's needs by adding or removing a set of rigid stays located within the anterior support.

Referring now the drawings, in which like numerals indicate like elements throughout the several figures, illustrative embodiments of the invention will be described below with reference to the appended drawings.

Turning now to FIG. 1, a lumbo-sacral orthopedic brace 10 comprises an anterior support 100, a posterior support 200, and a set of connection straps 300. The anterior support 100 and posterior support 200 are formed of a soft breathable material. The anterior support 100 and posterior support 200 are removably attached to each other through the use of the set of connection straps 300 that may be adjustably positioned in order to fit patients of varying forms and sizes.

The anterior support 100 has front 102 and rear sides 104 made of a hook and loop material, such as VELCRO, defining a large cavity 106. Within this cavity are located a plurality of pockets 110, formed by a series of soft flexible webs 108 connected on the sides and the bottom to the rear side 104 of the anterior flexible support 100. An expanded view of the anterior support 100 detailing the placement of the pockets 110 may be seen in FIG. 1A.

Returning to FIG. 1, a plurality of lightweight polymer stick-shaped splints 400 may be inserted into the plurality of pockets 110 in order to limit motion. As a patient's need for lumbo-sacral support decreases, the polymer stick-shaped splints 400 may be removed one by one in order to provide the proper amount of support. The polymer stick-shaped splints 400 may also be used in conjunction with a single large splint 602 inserted into large cavity 106 to provide an even greater level of support. This ensures that the amount of support provided by the brace 10 may be matched exactly to a patient's individual requirements.

The posterior support comprises a front side 202 and a back side 204 formed of a hook and loop material. The posterior support 200 incorporates a cavity within the posterior support 200 sized to accept a rigid splint 206. This would allow a patient to vary the bracing provided by the posterior support as needed.

The flexible anterior 100 and posterior 200 supports, as well as the lateral stays 500 and thoracic lumbar support 700, may be made of a soft breathable material, such as ORTHO-WICK, laminated to a foam with a loop material outer layer. This provides a breathable material which is cool and flexible to enhance a patient's comfort and which will fit a patient snugly. Further, such a material may be readily adjusted to form a soft body jacket that may apply the forces desired to immobilize specific types of motion in specific patients. Although in an illustrative embodiment the polymer splints 400 are made of a high-density polyethylene material, they may be made of any substantially rigid or semi-rigid material including various metals without departing from the spirit or scope of the invention.

The set of connection straps 300 secure anterior support 100 and posterior support 200 together to form the completed brace 10. Each side of the anterior support 100 and posterior support 200 is connected to the other by a set of these connection straps 300. Each set of connection straps 300 has a first crosspiece 302 and a second crosspiece 304, both formed of a hook and loop material such as VELCRO. The first crosspiece 302 is attached to the edge of posterior support 200 and the second crosspiece 304 is attached to the edge of the anterior support 100.

In an illustrative embodiment, the first crosspiece 302 comprises a set of loops 306 through which a series of flexible straps 310 pass. Each strap 310 is attached to the second crosspiece 304 with a nylon strip 312. Each flexible strap 310 passes through one of the set of loops 306 after which a group of flexible straps 310 is attached to a common strap 318 made of a hook and loop material. In the illustrative embodiment, two flexible straps 310 pass through two loops 306 and are coupled to one of a number of common straps 318. Each common strap 318 is pulled back over flexible straps 310 and attached at any angle to either second crosspiece 304 or anterior support 100 in order to tighten the set of connection straps 300 and connect the anterior support 100 and posterior support 200 together and thereby secure the brace 10 to the patient.

The set of connection straps 300 further comprises a rigid strap 314 attached to anterior support 100 with nylon strip 312, and passing through one of said plurality of loops 306. Unlike the plurality of flexible straps 310, rigid strap 314 is not attached to one of the common straps 318 after passing through the loop, but instead may be freely positioned or removed from the loop. Like common strap 318, rigid strap 314 is folded back over flexible straps 310 and attached to the second crosspiece 304 or to anterior support 100. Rigid strap 314 thus covers the flexible straps 310, minimizing their flexibility and locking out unwanted motion. As with common strap 318 detailed above, the rigid strap may be attached at any angle to the anterior support (or to second crosspiece 304), thereby ensuring that the fitting of brace 10 may be tailored to a patient of any size or shape. The illustrative embodiment is shown with two sets of flexible straps 310 and two rigid straps 314. It will be appreciated by those skilled in the art that more or less sets of flexible straps and/or rigid straps may be used without departing from the spirit or letter of the invention.

Referring now to FIG. 2, a lateral expansion panel 500 is illustrated that, when coupled with brace 10 shown in FIG. 1, substantially increases the circumference of the brace. Lateral panel 500 comprises front side 502 and back side 504 made of a hook and loop material. A pair of straps 510 is fastened to an edge of the lateral panel. The straps 510 may be adjustably connected at any angle to any portion of the anterior support, while the rear side 504 of lateral panel 500 may be engaged at any angle by the connection straps 300. This allows a patient to vary the angle at which lateral panel 500 rests when brace 10 is worn, thereby ensuring a closer fit. Further, because straps 510 may be attached to any portion of the anterior support 100, the effective size of the brace 10 may be increased or decreased by varying the point at which the lateral panel 500 is connected to the anterior support in order to account for patients of different sizes.

Two lateral panels 500 may be combined on a single side of the brace by attaching the straps 510 of one lateral panel to the straps of the second lateral panel, then attaching the second lateral panel to the anterior support of the brace 10. When combined with connecting straps 300 described with respect to FIG. 1, the overall effect of lateral panel 500 is to allow a lumbo-sacral brace to fit any patient ranging from the extremely small to the especially large.

Additionally, lateral panel 500 comprises a cavity 506 defined by the front side 502 and back side 504 of lateral panel 500. Cavity 506 may contain a rigid lateral splint 508. Rigid lateral splint 508 affords additional protection to the side of an injured patient as well as serving as yet another means of eliminating unwanted torso motion.

Referring now to FIG. 3, a lumbo-sacral brace 10 incorporating a thoracic lumbar support member 700 and sternal extension 600 is shown. The thoracic lumbar support 700 provides additional bracing for the upper back. The sternal extension 600 allows the brace to limit the forward flexion motion of the torso, working in tandem with the thoracic lumbar support.

The lumbar support 700 comprises a y-shaped padded body 702, a bottom flap 704, and flexible straps 706. The y-shaped padded body 702 of the thoracic lumbar support 700 is formed of a soft, flexible material and has a front side 712 and back side 714. A cavity 710 is formed by the front and back sides, with the mouth of the cavity located at the bottom of the y-shaped padded body 702. A lightweight polymer splint 716 may be inserted within the cavity 710 in order to minimize backward motion of the upper back providing additional thoracic support. In an illustrative embodiment, the splint 716 is fixed within cavity 710 and may not be removed. However, alternate embodiments may allow the splint 716 to be removed and inserted at will in order to provide for varying degrees of support and minimization of motion.

The bottom flap 704 is connected to padded body 702 and is made of a hook and loop material such as VELCRO. Bottom flap 704 is affixed to the back side 714 of the padded body 702. The bottom flap 704 may be attached to the back side 204 of posterior support 200 at any height or angle. Thus, the thoracic lumbar support 700 may be adjusted to support each patient individually.

Flexible straps 706 are formed of a hook and loop material and connected to each branch of y-shaped padded body 702, as shown in FIG. 3. Each of flexible straps 706 contain a hook strip 718 that may be adjustably positioned anywhere on the flexible strap. Hook strip 718 is typically positioned so that flexible straps 706 may be extended and doubled back in such a fashion that the end of the flexible strap is held to the hook strip. This allows flexible straps 706 to pass through or around a loop, ring, or other object and still attach to hook strip 718.

Flexible straps 706 connect thoracic lumbar support 700 to sternal extension 600 shown in FIG. 3. The sternal extension 600 includes a rigid lightweight polymer splint 602, a connector rod 614, and a u-shaped padded body 604. The splint 602 is shaped to fit into the large cavity 106 of anterior support 100. The splint 602 provides additional support to eliminate forward flexion motion of a patient's spine and abdomen, and may be used with the stick-shaped splints 400 described above with respect to FIG. 1 in cases where enhanced longitudinal support is necessary. One end of the connector rod 614 is fastened to the polymer splint 602, while the other end of the connector rod 614 is attached to the u-shaped padded body 604. The connector rod 614 is made of a rigid load-bearing material, preferably a lightweight metal. The u-shaped padded body 604 is sized such that the concave portion of the body fits snugly against the chest wall of a patient. A ring 606 is attached to the top of each branch of the u-shaped padded body 604. In an illustrative embodiment, flexible straps 706 pass through a plurality of sternal extension rings 606; each strap passes through a separate ring and then is folded back over itself to connect to hook strip 718. Flexible straps 706 may be pulled in order to tighten the fit of sternal extension 600 and thoracic lumbar support 700. The flexible straps adhere to hook strips 718 in order to maintain the fit chosen for each patient.

In another embodiment of the present invention, as shown in FIG. 4, twelve lacing loops 810 are provided along the edge of the first crosspiece 302 which is attached to the posterior support 200. It should be understood that the number of lacing loops 810 may vary based on the design of the brace 10.

Eight additional lacing loops 810 are located along the edge of the nylon strip 814 attached to the second crosspiece 304. The second crosspiece 304 is formed of hook and loop material which attaches to the lateral edge of the anterior support 100. It should be understood that the second crosspiece 304 may also attach to the edge of the lateral panel 500 if provided with the anterior panel 100.

As shown in FIG. 4, each lateral panel 500 comprises the cavity 506. Rigid splints 508 are positioned in the cavity 506 to provide additional protection to the sides of the patient.

The posterior panel is connected to the anterior panel by two continuous lacings 820. It is preferable to use a nylon cord for the lacing 820 which provide resiliency and strength. Each lacing 820 passes through six adjacent lacing loops 810 attached to the posterior support 200 and four adjacent lacing loops 810 attached to the nylon strip 814. Each lacing is joined to an attachment strap 824 through three lacing loops 810 connected to the attachment strap 824. The ends of the lacings 820 are joined at the lacing loops of the attachment strap 824 forming a continuous loop. The lacings 820 can be joined by chemical or heat bonding means. One side of the attachment strap is covered with hook fastening material.

In order to properly fit the brace 10, a user can remove the second crosspiece 304 from the anterior support 100. This allows the user to easily slip the brace 10 around the waist rather than slipping it over the user's head. After properly positioning the brace 10 on the user's torso, the second crosspiece 304 is re-attached to the anterior support 100 using the hook and loop material attachment. The user then grips each attachment strap 824 and pulls until achieving a snug fit and proper support for the back. This action tightens the brace 10 by adjusting the lacings 820. The hook material located on the attachment straps 824 are used to attach the attachment straps 824 to the anterior support 100.

When the user desires to remove the brace 10, the user simply releases the attachment straps 824 from the anterior support 100. This action loosens the lacings 820 allowing the user to remove one of the second crosspieces 304 from the anterior support 100 and remove the entire brace 10. Those skilled in the art will understand that the use of lacings 820 with the attachment straps 824 provides easy adjustment of the tension of the brace 10.

In the embodiment of FIG. 4, the splint 602 can be placed in the cavity 106 of the anterior support 100 and secured using closure tab 836. One side of the closure tab 836 is covered with hook-type material which attaches to the loop material covering the anterior support 100, sealing the cavity 106. Similarly, the rigid splint 206 can be secured in the cavity 203 using closure tabs 840. Lateral splints 508 can be secured inside the cavity 506 of the lateral panels 500 using closure tabs 845. It should be understood that closure tabs 840, 845 also have one side covered with hook material which is used to seal cavities 203, 506, similar to closure tab 836.

The brace 10 is made to simulate the viscoelastic qualities of the human body while combining the best features of a soft corset with those of a rigid plastic body jacket and to form-fit the supports to the patient. This allows the supports to minimize undesired spinal motion and still provide a comfort level suitable for long-term wear. The brace 10 may be custom fitted to different types of patients without alterations or modifications beyond those readily performed by hand, and without physically altering or manipulating the dimensions of any portion of the brace. The brace 10 is lightweight and fits patients of all heights and weights. However, the illustrative embodiment described above and displayed in FIGS. 1–4 should be considered to be an example of one of many possible forms for the invention, rather than displaying the sole embodiment of the invention. Accordingly, the figures and above description are intended by way of illustration rather than limitation, and alternate methods of practicing the invention will occur to those skilled in the art upon reading the specification without departing from the spirit or the letter of the claims.

We claim:
1. A thoraco-lumbo-sacral orthopedic brace comprising:
an anterior flexible member shaped to fit over the front of a patient's torso having a front side and a rear side defining a cavity of said anterior flexible member;
a plurality of pockets located within said cavity and on the rear side of said cavity of said anterior flexible member;
a posterior flexible member shaped to fit over the rear of a patient's torso;
a plurality of substantially rigid stick shaped splints positioned within said plurality of pockets of said anterior flexible member;
a single rigid splint inserted in said cavity, which single rigid splint operates in conjunction with said plurality of substantially rigid stick shaped splints to minimize the forward flexibility of said brace; and
a plurality of flexible straps to interconnect the anterior flexible member and the posterior flexible member.

2. A lateral panel for expanding the size of a back brace, comprising:
a generally rectangular member having front and back sides defining a cavity, said front side formed of a hook and loop material;
a substantially rigid splint located within the cavity; and
a flexible strap formed of a hook and loop material.

3. The panel of claim 2, further comprising top and bottom edges defining a slot located at the top of said cavity, said substantially rigid splint removable through said slot.

4. A thoraco-lumbo-sacral orthopedic brace comprising:
an anterior flexible member shaped to fit over the front of a patient's torso and being formed of a hook and loop material;
a posterior flexible member shaped to fit over the rear of a patient's torso and being formed of a hook and loop material; and
a flexible lateral panel formed of a hook and loop material comprising:
front and back sides defining a cavity, said back side attached to said posterior flexible member; and
a plurality of flexible straps to interconnect the anterior flexible member, the posterior flexible member, and the flexible lateral panel.

5. The brace of claim 4, wherein said flexible lateral panel may be adjustably positioned to attach to any portion of said anterior flexible member.

6. The brace of claim 4, further comprising a second flexible lateral panel formed of a hook and loop material, wherein the plurality of flexible straps of the second lateral panel is attached to the plurality of flexible straps of the first lateral panel, and the back side of the second lateral panel is attached to said anterior flexible member.

7. The brace of claim 4, further comprising a substantially rigid splint located within the cavity of the lateral panel.

8. An apparatus for securing a brace, comprising:
a first crosspiece;
a second crosspiece;
a first plurality of loops attached to the first crosspiece;
a second plurality of loops attached to the first crosspiece,
a first plurality of flexible straps attached to the second crosspiece and passing through said first plurality of loops;
a second plurality of flexible straps attached to the second crosspiece and passing through said second plurality of loops;
a first rigid strap attached to the second crosspiece and passing through said first plurality of loops; and a second rigid strap attached to the second crosspiece and passing through said second plurality of loops.

9. The apparatus of claim 8, wherein said first and second rigid straps restricts the motion of said first and second plurality of flexible straps.

10. A thoraco-lumbo-sacral orthopedic brace comprising:
   an anterior flexible member shaped to fit over the front of a patient's torso having a front side of said anterior flexible member having the surface thereof formed of hook and loop material and a rear side of said anterior flexible member, said front side of said anterior flexible member and said rear side of said anterior flexible member defining a cavity of the anterior flexible member, wherein said anterior flexible member has a first edge portion of said anterior flexible member and a second edge portion of said anterior flexible member;
   a sternal extension member comprising:
      a substantially rigid insert sized to fit within said cavity of said anterior flexible member;
      a concave padded cushion;
      a first ring connected to said concave padded cushion;
      a second ring connected to said concave padded cushion; and
      a rigid bar connecting said concave padded cushion to said substantially rigid anterior insert;
   a posterior flexible member shaped to fit over the rear of a patient's torso and having a first edge portion of said posterior flexible member and a second edge portion of said posterior flexible member, and having a front side of said posterior flexible member being formed of hook and loop material and a rear side of said posterior flexible member, said front side of said posterior flexible member and said rear side of said posterior flexible member defining a cavity of the posterior flexible member;
   a rigid posterior insert sized to fit within said cavity of said posterior flexible member;
   a thoracic lumbar support comprising:
      a y-shaped padded body with first and second sides defining an interior cavity of the y-shaped padded body, and wherein the y-shaped padded body has a first extension and a second extension;
      a bottom flange formed of hook and loop material and connected to said posterior flexible member;
      a first flexible strap formed of a hook and loop material connected to said first extension, and adjustably connected to said first ring; and
      a second flexible strap formed of a hook and loop material connected to said second extension, and adjustably connected to said second ring;
   a first plurality of flexible straps attached to said edge portion of said posterior flexible member;
   a second plurality of flexible straps attached to said second edge portion of said posterior flexible member;
   a first plurality of loops attached to said first edge portion of said anterior flexible member and having each one of said first plurality of flexible straps passing through each of said first plurality of loops; and
   a second plurality of loops attached to said first edge portion of said anterior flexible member and having each one of said second plurality of flexible straps passing through each of said second plurality of loops.

11. The brace of claim 10, wherein the bottom flange of the thoracic lumbar support may be connected to any point of the posterior flexible member.

12. The brace of claim 10, further comprising a substantially rigid splint located within said interior cavity of said y-shaped padded body.

13. An apparatus for providing thoracic lumbar support, comprising:
   a y-shaped padded body with first and second sides defining an interior cavity, and having first and second extensions;
   a bottom flange formed of hook and loop material, connected to said first side;
   a first flexible strap formed of a hook and loop material connected to said first extension;
   a second flexible strap formed of a hook and loop material connected to said second extension.

14. The apparatus of claim 13, further comprising a substantially rigid insert located within said cavity.

15. A thoraco-lumbo-sacral orthopedic brace comprising:
   an anterior flexible member shaped to fit over the front of a patient's torso having a front side and a rear side defining a cavity of said anterior flexible member, and having first and second edge portions, said front side having the surface thereof formed of hook and loop material;
   a sternal extension member comprising:
      a substantially rigid anterior insert sized to fit within said [anterior] cavity of said anterior flexible member;
      a concave padded cushion;
      a first ring connected to said concave padded cushion;
      a second ring connected to said concave padded cushion; and
      a rigid bar connecting said concave padded cushion to said substantially rigid anterior insert;
   a posterior flexible member shaped to fit over the rear of a patient's torso and having first and second edge portions, and having front and rear sides defining a cavity of said posterior flexible member, said front side being formed of hook and loop material;
   a rigid posterior insert sized to fit within said cavity of said posterior flexible member;
   thoracic lumbar support comprising:
      a y-shaped padded body with first and second sides defining an interior cavity of the y-shaped padded body, and having first and second extensions;
      a bottom flange formed of hook and loop material and connected to said posterior flexible member;
      a first flexible strap formed of a hook and loop material connected to said first extension, and adjustably connected to said first ring; and
      a second flexible strap formed of a hook and loop material connected to said second extension, and adjustably connected to said second ring;
   a first and second means for interconnecting said anterior flexible member and said posterior flexible member, each of said first and second means comprising:
      a first crosspiece attached to an edge portion of said posterior flexible member;
      a second crosspiece attached to an edge portion of said anterior flexible member;
      a first plurality of loops attached to said first crosspiece;
      a second plurality of loops attached to said second crosspiece
      a plurality of lacings connecting said first crosspiece to said second crosspiece through said first plurality of loops and said second plurality of loops; and
      a plurality of attachment straps connected to said lacings.

16. The brace of claim 15, wherein the bottom flange of the thoracic lumbar support may be connected to any point of the posterior flexible member.

17. The brace of claim 15, further comprising a substantially rigid splint located within said interior cavity of said y-shaped padded body.

18. A thoraco-lumbo-sacral orthopedic brace comprising:
an anterior flexible member shaped to fit over the front of a patient's torso and being formed of a hook and loop material;
a posterior flexible member shaped to fit over the rear of a patient's torso and being formed of a hook and loop material; and
a first flexible lateral panel formed of a hook and loop material comprising:
first front and back sides defining a first cavity and
a first plurality of flexible straps attached to the first flexible lateral panel for attaching said first flexible lateral panel to said anterior or posterior flexible member; and
a first plurality of flexible interconnecting straps to interconnect the first flexible lateral panel to the opposite posterior or anterior flexible member.

19. The brace of claim 18, wherein said first flexible lateral panel may be adjustably positioned to attach to any portion of said anterior or posterior flexible member.

20. The brace of claim 18, further comprising a first substantially rigid splint located within the first cavity of the first flexible panel.

21. The brace of claim 18, further comprising a second flexible lateral panel formed of a hook and loop material and having front and back sides defining a second cavity and a second plurality of flexible straps attached to the second flexible lateral panel for attaching said second flexible lateral panel to said anterior or posterior flexible member and a second plurality of flexible interconnecting straps, wherein the second plurality of flexible straps attached to the second lateral panel is attached to the flexible anterior or posterior member, and the second plurality of flexible interconnecting straps interconnect the second flexible lateral panel to the opposite posterior or anterior flexible member.

22. The brace of claim 21, wherein said first flexible lateral stay and the second flexible lateral panel may be adjustably positioned to attach to any portion of said anterior or posterior flexible member.

23. The brace of claim 21, further comprising a first and a second substantially rigid splints located respectively within the first and second cavities of the first and second flexible panels.

* * * * *